United States Patent
Peine

(10) Patent No.: US 11,406,464 B2
(45) Date of Patent: Aug. 9, 2022

(54) HANDLE ASSEMBLIES FOR ROBOTIC SURGICAL SYSTEMS

(71) Applicant: Covidien LP, Mansfield, MA (US)

(72) Inventor: William Peine, Ashland, MA (US)

(73) Assignee: Covidien LP, Mansfield, MA (US)

( * ) Notice: Subject to any disclaimer, the term of this patent is extended or adjusted under 35 U.S.C. 154(b) by 440 days.

(21) Appl. No.: 16/615,614

(22) PCT Filed: May 7, 2018

(86) PCT No.: PCT/US2018/031342
§ 371 (c)(1),
(2) Date: Nov. 21, 2019

(87) PCT Pub. No.: WO2018/217435
PCT Pub. Date: Nov. 29, 2018

(65) Prior Publication Data
US 2020/0170733 A1    Jun. 4, 2020

Related U.S. Application Data

(60) Provisional application No. 62/511,457, filed on May 26, 2017.

(51) Int. Cl.
*A61B 34/37* (2016.01)
*A61B 34/00* (2016.01)

(52) U.S. Cl.
CPC .............. *A61B 34/37* (2016.02); *A61B 34/25* (2016.02); *A61B 34/74* (2016.02); *A61B 34/76* (2016.02)

(58) Field of Classification Search
CPC ... A61B 2090/067; A61B 34/25; A61B 34/37; A61B 34/74; A61B 34/76
See application file for complete search history.

(56) References Cited

U.S. PATENT DOCUMENTS

| | | |
|---|---|---|
| 4,760,848 A | 8/1988 | Hasson |
| 5,626,608 A | 5/1997 | Cuny et al. |
| 8,828,023 B2 | 9/2014 | Neff et al. |

(Continued)

FOREIGN PATENT DOCUMENTS

| | | |
|---|---|---|
| WO | 2013018934 A1 | 2/2013 |
| WO | 2017210501 A1 | 12/2017 |

OTHER PUBLICATIONS

Japanese Office Action dated Dec. 27, 2021 corresponding to counterpart Patent Application JP 2019-565304.

(Continued)

*Primary Examiner* — Insa Sadio
(74) *Attorney, Agent, or Firm* — Carter, DeLuca & Farrell LLP

(57) ABSTRACT

A robotic surgical system includes a robotic arm and a user interface. The robotic arm supports a jaw assembly that includes opposed jaw members defining a jaw angle therebetween. The user interface includes a handle assembly having a body portion, a handle controller disposed within the body portion, and a first actuator movable relative to the body portion to change an opening angle of the first actuator. The first actuator has a force profile which is a force required to move the first actuator as a function of the opening angle, and the jaw assembly has a jaw angle profile which is the jaw angle as a function of the opening angle.

17 Claims, 6 Drawing Sheets

(56) References Cited

U.S. PATENT DOCUMENTS

| | | | |
|---|---|---|---|
| 2004/0186345 A1* | 9/2004 | Yang | A61B 34/77 600/102 |
| 2009/0245600 A1* | 10/2009 | Hoffman | H04N 13/366 348/240.99 |
| 2011/0015632 A1 | 1/2011 | Artale | |
| 2013/0103050 A1 | 4/2013 | Richmond et al. | |
| 2013/0175319 A1 | 7/2013 | Felder et al. | |
| 2013/0274922 A1 | 10/2013 | Nixon | |
| 2014/0160015 A1 | 6/2014 | Ogawa et al. | |
| 2018/0310999 A1 | 11/2018 | Peine | |
| 2020/0015917 A1 | 1/2020 | Cavalier et al. | |
| 2020/0315729 A1 | 10/2020 | Blanco et al. | |

OTHER PUBLICATIONS

Extended European Search Report dated Feb. 4, 2021 corresponding to counterpart Patent Application EP 18806893.6.
International Search Report dated Aug. 29, 2018 and Written Opinion completed Aug. 29, 2018 corresponding to counterpart Int'l Patent Application PCT/US2018/031342.
Indian Office Action dated Feb. 24, 2022 corresponding to counterpart Patent Application IN 201917045590.

\* cited by examiner

HANDLE ASSEMBLIES FOR ROBOTIC SURGICAL SYSTEMS

CROSS-REFERENCE TO RELATED APPLICATIONS

This application is a National Stage Application of PCT/US2018/031342, filed May 7, 2018 under 35 USC § 371 (a), which claims benefit of and priority to U.S. Provisional Patent Application Ser. No. 62/511,457 filed May 26, 2017, the disclosures of each of the above-identified applications are hereby incorporated by reference in their entirety.

BACKGROUND

Robotic surgical systems have been used in minimally invasive medical procedures. During such medical procedures, a robotic surgical system is controlled by a surgeon interfacing with a user interface. The user interface allows the surgeon to manipulate an end effector of a robot system that acts on a patient. The user interface includes a control arm assembly having a handle assembly that is moveable by the surgeon to control the robotic surgical system.

There is a need for improved handle assemblies for controlling the end effector of the robotic system.

SUMMARY

The present disclosure relates generally to handle assemblies of a user interface of a robotic surgical system including finger-controller actuators configured to allow a clinician to control an end effector of a robot system of the robotic surgical system during a surgical procedure.

In one aspect of the present disclosure, a robotic surgical system includes a robotic arm and a user interface. The robotic arm supports a jaw assembly including opposed jaw members defining a jaw angle therebetween. The user interface includes a handle assembly having a body portion, a handle controller disposed within the body portion, and a first actuator movable relative to the body portion to change an opening angle of the first actuator. The first actuator has a force profile which is a force required to move the first actuator as a function of the opening angle, and the jaw assembly has a jaw angle profile which is the jaw angle as a function of the opening angle.

In aspects, the jaw angle profile defines a jaw angle curve, and a microcontroller of the handle controller is configured to transmit the opening angle of the first actuator to the robotic arm to effect a change in the jaw angle of the jaw members based on the jaw angle curve. The jaw angle curve may be linear such that, for example, as the opening angle of the first actuator decreases, the jaw angle of the jaw members decreases.

In aspects, the force profile defines a force curve, and a microcontroller of the handle controller is configured to record the opening angle of the first actuator and adjust operating parameters of a motor of the handle controller to effect a change in the force required to actuate the first actuator based on the force curve. In some aspects, a portion of the force curve has a negative slope in which the force increases as the opening angle decreases. In certain aspects, a portion of the force curve has a positive to negative slope transition point at a predetermined opening angle of the first actuator such that the motor produces a torque to maintain the first actuator at the predetermined opening angle.

The first actuator may have an open position in which the opening angle is a first open angle and a closed position in which the opening angle is a second open angle less than the first open angle. In some aspects, the force profile has a first region defined between the first open angle and a third open angle that is less than the first open angle and greater than the second open angle. The jaw members may have a fully open position and a fully closed position. The jaw members may be disposed in the fully open position when the opening angle of the first actuator is at the first open angle and in the fully closed position when the opening angle of the first actuator is at the third open angle.

In certain aspects, the force profile has a second region defined between the second open angle and the third open angle, and the jaw members are disposed in an over-closed position when the opening angle of the first actuator is between the second and third open angles. In particular aspects, the force profile has a third region in which the opening angle of the first actuator is greater than the first open angle, and the jaw members are disposed in an over-open position when the opening angle of the first actuator is greater than the first open angle.

The first region of the force profile may be linear and have a first negative slope such that the force increases as the opening angle decreases in the first region. In some aspects, the second region of the force profile is linear and has a second negative slope that is greater than the first negative slope of the first region. In certain aspects, the third region of the force profile is linear and has a third negative slope that is greater than the first negative slope of the first region, and when no force is applied to the first actuator, the first actuator is biased towards the first open angle.

The second region may include a torque transition point at a predetermined opening angle of the first actuator such that when the first actuator is moved to the predetermined opening angle, the motor of the handle controller produces a torque to maintain the first actuator at the predetermined opening angle.

The first region of the force profile may be non-linear. In some aspects, the first region of the force profile includes a positive to negative torque transition point at a predetermined opening angle of the first actuator such that when the first actuator is moved to the predetermined opening angle, the motor of the handle controller produces a torque to maintain the first actuator at the predetermined opening angle.

Other aspects, features, and advantages will be apparent from the description, drawings, and the claims.

BRIEF DESCRIPTION OF THE DRAWINGS

Various aspects of the present disclosure are described herein below with reference to the drawings, which are incorporated in and constitute a part of this specification, wherein.

DETAILED DESCRIPTION

Figure 1:
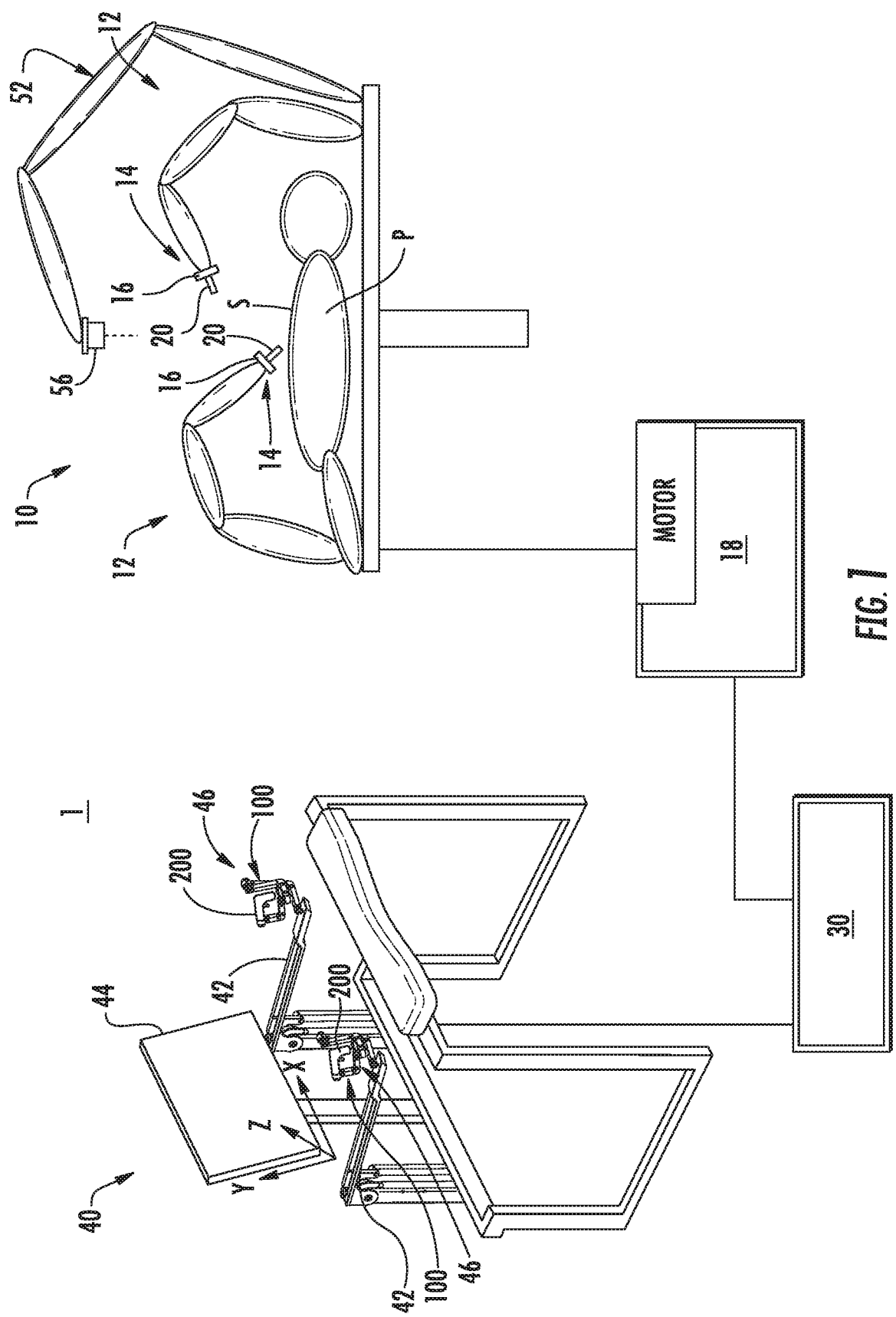
FIG. 1 is a schematic illustration of a robotic surgical system including a robot system and a user interface having two control arm assemblies in accordance with an embodiment of the present disclosure.

Embodiments of the present disclosure are now described in detail with reference to the drawings in which like reference numerals designate identical or corresponding elements in each of the several views. As used herein, the term "clinician" refers to a doctor (e.g., a surgeon), nurse, or any other care provider and may include support personnel. Throughout this description, the term "proximal" refers to a portion of a system, device, or component thereof that is closer to a clinician, and the term "distal" refers to a portion of the system, device, or component thereof that is farther from the clinician.

Turning now to FIG. 1, a robotic surgical system 1 in accordance with the present disclosure is shown. The robotic surgical system 1 includes a robot system 10, a processing unit 30, and an operating console or user interface 40. The robot system 10 generally includes linkages 12 and a robot base 18. The linkages 12 moveably support an end effector or tool 20 which is configured to act on tissue of a patient "P" at a surgical site "S". The linkages 12 may form arms, each arm 12 having an end 14 that supports the tool 20. In addition, the ends 14 of each of the arms 12 may include an imaging device 16 for imaging the surgical site "S", and/or a tool detection system (not shown) that identifies the tool 20 (e.g., a type of surgical instrument) supported or attached to the end 14 of the arm 12.

The processing unit 30 electrically interconnects the robot system 10 and the user interface 40 to process and/or send signals transmitted and/or received between the user interface 40 and the robot system 10, as described in further detail below.

The user interface 40 includes a display device 44 which is configured to display three-dimensional images. The display device 44 displays three-dimensional images of the surgical site "S" which may include data captured by imaging devices 16 positioned on the ends 14 of the arms 12 and/or include data captured by imaging devices that are positioned about the surgical theater (e.g., an imaging device positioned within the surgical site "S", an imaging device positioned adjacent the patient "P", an imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices 16, 56 transmit captured imaging data to the processing unit 30 which creates three-dimensional images of the surgical site "S" in real-time from the imaging data and transmits the three-dimensional images to the display device 44 for display.

The user interface 40 includes control arms 42 which support control arm assemblies 46 to allow a clinician to manipulate the robot system 10 (e.g., move the arms 12, the ends 14 of the arms 12, and/or the tools 20). The control arm assemblies 46 are in communication with the processing unit 30 to transmit control signals thereto and to receive feedback signals therefrom which, in turn, transmit control signals to, and receive feedback signals from, the robot system 10 to execute a desired movement of robot system 10.

Each control arm assembly 46 includes a gimbal 100 operably coupled to the control arm 42 and an input device or handle assembly 200 operably coupled to the gimbal 100. For a detailed description of the structure and function of exemplary gimbals, reference may be made to commonly owned U.S. Provision Patent Application Ser. No. 62/345,505 ("the '505 application), entitled "CONTROL ARM ASSEMBLIES FOR ROBOTIC SURGICAL SYSTEMS", filed Jun. 3, 2016, the entire contents of which are incorporated herein by reference.

Each of the handle assemblies 200 is moveable through a predefined workspace within a coordinate system having "X", "Y", and "Z" axes to move the tool 20, the arm 12, and/or the end 14 of the arm 12 within a surgical site "S". The three-dimensional images on the display device 44 are orientated such that the movement of the gimbals 100, as a result of the movement of the handle assemblies 200, moves the ends 14 of the arms 12 as viewed on the display device 44. It will be appreciated that the orientation of the three-dimensional images on the display device 44 may be mirrored or rotated relative to a view from above the patient "P". In addition, it will be appreciated that the size of the three-dimensional images on the display device 44 may be scaled to be larger or smaller than the actual structures of the surgical site "S" to permit a clinician to have a better view of structures within the surgical site "S". For a detailed discussion of scaling of handle assembly movement, reference may be made to commonly owned International Application No. PCT/US16/65588, filed Dec. 8, 2016, the entire contents of which are incorporated herein by reference.

For a detailed discussion of the construction and operation of a robotic surgical system 1, reference may be made to U.S. Pat. No. 8,828,023, the entire contents of which are incorporated herein by reference.

Figure 2:
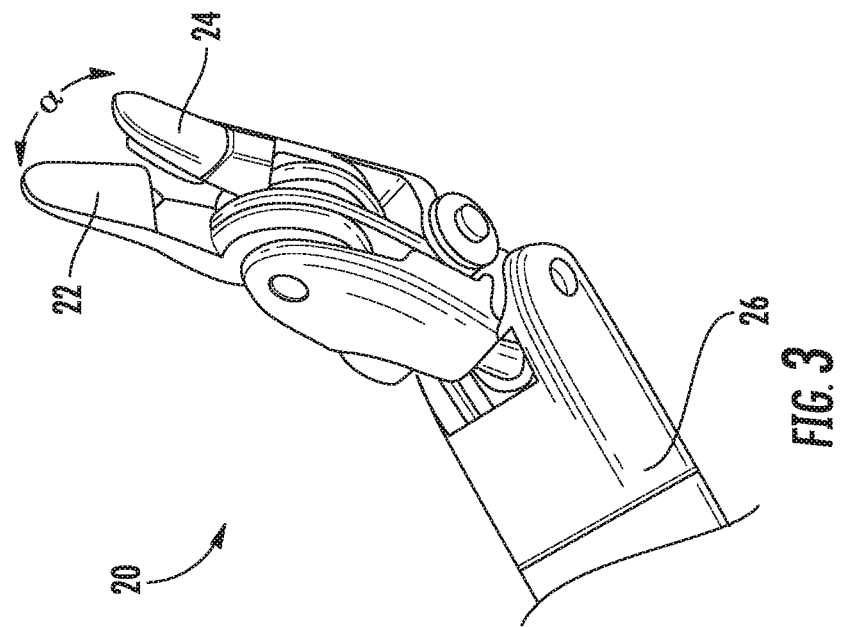
FIG. 2 is a perspective view of a handle assembly of one of the control arm assemblies of the user interface of the robotic surgical system of FIG. 1, with a hand of a clinician shown in phantom.

Referring now to FIG. 2, the handle assembly 200 of each of the control arm assemblies 46 (FIG. 1) includes a body portion 210 and a grip portion 220. The body portion 210 includes a housing 212 supporting a plurality of actuators 214, 216, 218 for controlling various functions of the tool 20 (FIG. 1) of the robot system 10. As illustrated and oriented in FIG. 2, the first actuator 214 is disposed on an outer side surface 212a of the housing 212, the second actuator 216 is disposed on a top surface 212b of the housing 212, and the third actuator 218 extends from a bottom surface 212c of the housing 212 to form a trigger. It should be understood that the actuators 214, 216, 218 can have any suitable configuration (e.g., paddles, buttons, knobs, toggles, slides, rockers, etc.), and placement of the actuators 214, 216, 218 about the handle assembly 200 may vary. The first actuator 214 is shown in the form of a paddle including a finger rest 222 and a strap 224 extending over the finger rest 222 to secure a finger (e.g., the index finger "I") of the clinician's hand "H" (shown in phantom) to the first actuator 214.

Each handle assembly 200 allows a clinician to manipulate (e.g., clamp, grasp, fire, open, close, rotate, thrust, slice, etc.) the respective tool 20 (FIG. 1) supported at the end 14 of the arm 12 of the robot system 10. As shown, for example, in FIG. 3, the tool 20 may have a jaw assembly including opposed jaw members 22, 24 extending from a tool shaft 26. The first actuator 214 (FIG. 2) may be configured to actuate the jaw members 22, 24 of the tool 20 between open and closed configurations, as described in further detail below. The second and third actuators 216, 218 (FIG. 2) can effect other functions of the tool 20, such as fixing the configuration of the jaw members 22, 24 relative to one another, rotating the jaw members 22, 24 relative to the tool shaft 26, firing a fastener (not shown) from one of the jaw members 22, 24, actuating a knife (not shown) disposed within one of the jaw members 22, 24, activating a source of electrosurgical energy such that electrosurgical energy is delivered to tissue via the jaw members 22, 24, among other functions within the purview of those skilled in the art.

Figure 4:
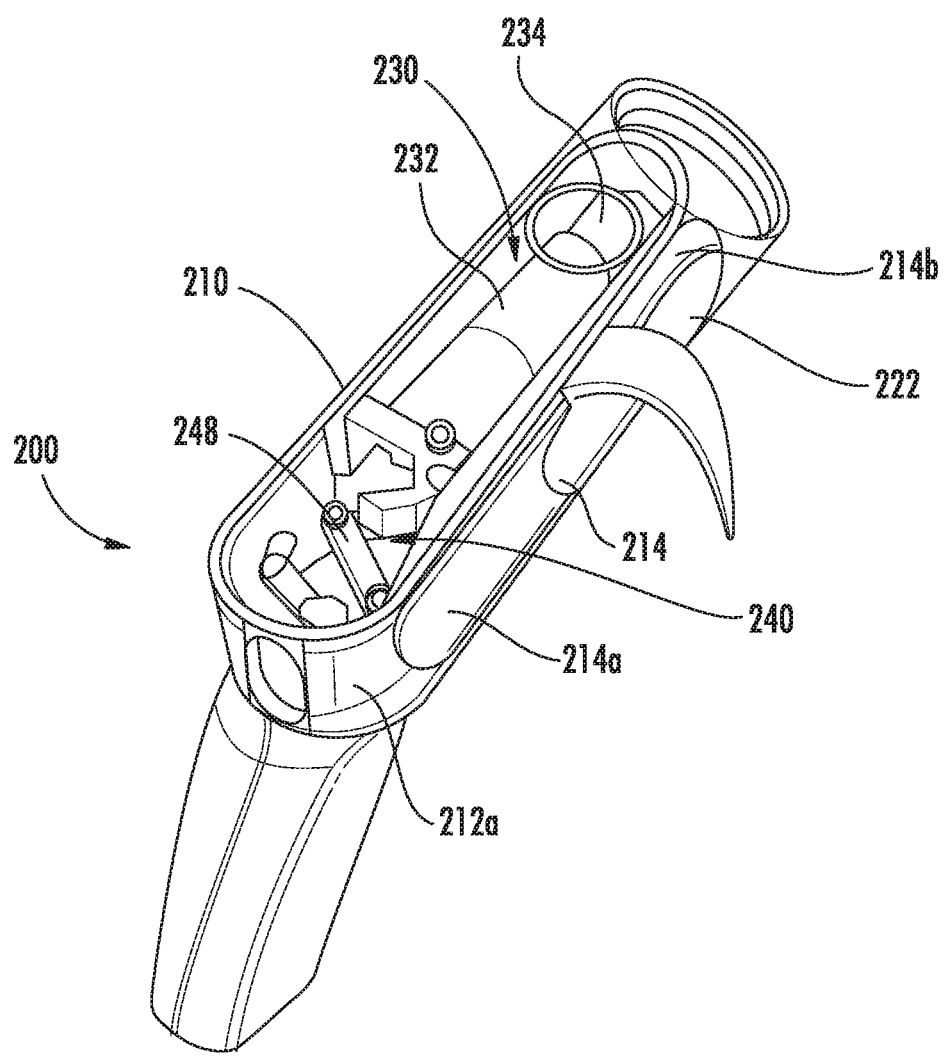
FIG. 4 is a top, perspective view, with parts removed, of the handle assembly of FIG. 2.

As shown in FIG. 4, a handle controller 230, including a motor 232 and a microcontroller 234, is disposed within the body portion 210 of the handle assembly 200. The handle controller 230 is activated by actuation of the first, second, and/or third actuators 214, 216, 218 (FIG. 2). The handle controller 230 converts mechanical movement of the first, second, and/or third actuators 214, 216, 218 into electrical signals which are sent to the microcontroller 234 which, in turn, records the positional movement (e.g., the angular position) of the first, second, and/or third actuators 214, 216, 218. The microcontroller 234 transmits the recorded positional movement to the processing unit 30 (FIG. 1) which, in turn, transmits electrical control signals to the robot system 10 (FIG. 1) to actuate a function of the arm 12 and/or the tool 20 (FIG. 1). The processing unit 30 may also transmit electrical signals back to the handle controller 230 to adjust operating parameter(s) of the motor 232 (e.g., power, speed, and/or torque), or the microcontroller 234 may respond to changes in the positional movement of the first, second, and/or third actuators 214, 216, 218, to adjust the operating parameter(s) of the motor 232. It should be understood that the robot system 10 may send signals to the processing unit 30 and thus, to the handle controller 230 to provide feedback to a clinician operating the handle assembly 200.

The first actuator 214 is mechanically coupled to the handle controller 230 by a linkage assembly 240, e.g., a four-bar linkage. For a detailed discussion of the structure and function of exemplary actuators and four-bar linkages, reference may be made to the '505 application, the entire contents of which were previously incorporated by reference. The first actuator 214 includes a proximal portion 214a and a distal portion 214b including the finger rest 222. The first actuator 214 has a biased position, when no force is applied to the first actuator 214, where the distal portion 214b extends laterally from the outer side surface 212a of the housing 212 of the handle assembly 200 and the proximal portion 214a is flush with, or is disposed within, the outer side surface 212a, as shown in FIG. 4.

Referring back to FIG. 2, a clinician grips the handle assembly 200 such that the index finger "I" (shown in phantom) of the clinician's hand "H" rests upon the first actuator 214, the palm (not shown) of the clinician's hand "H" rests on the grip portion 220 of the handle assembly 200, and the thumb "T" and the middle finger "M" of the clinician's hand "H" are free to actuate the second and third actuators 216, 218, respectively. When a clinician presses on and applies force to the finger rest 222 of the first actuator 214, the first actuator 214 moves towards a closed position where the distal portion 214b (FIG. 4) of the first actuator 214 moves towards the body portion 210 of the handle assembly 200 causing the proximal portion 214a (FIG. 4) of the first actuator 214 to move laterally away from the body portion 210, resulting in a corresponding mechanical movement of the linkage assembly 240 which is converted into electronic signals by the handle controller 230, as discussed above. When a clinician releases the finger force from the first actuator 214 and/or pulls his or her index finger "I" away from the first actuator 214, the first actuator 21 moves back towards the biased, open position.

The amount of finger force applied to the first actuator 214 by a clinician moves the first actuator 214 from the biased, open position towards the closed position to affect the position of the jaw members 22, 24 (FIG. 3) with respect to each other. In embodiments, the first actuator 214 is configured such that in the biased position, the jaw members 22, 24 are in a fully open position and the angular position or opening angle of the first actuator 214, as measured by the handle controller 230, is about 20°. As force is applied to the first actuator 214, the jaw members 22, 24 move towards each other to reach a fully closed position. In the fully closed position, the opening angle of the first actuator 214 is about 5°.

Movement of the first actuator 214 is controlled by the clinician's finger force, as described above, as well as torque produced by the motor 232 of the handle controller 230. The motor torque pushes or pulls the first actuator 214 against or away from the clinician's finger, and allows a clinician to back drive the first actuator 214 and use it as an input device. Specifically, a positive torque pushes the first actuator 214 open and towards the clinician's finger, and a negative torque pulls the first actuator 214 closed and away from the clinician's finger.

Figure 3:
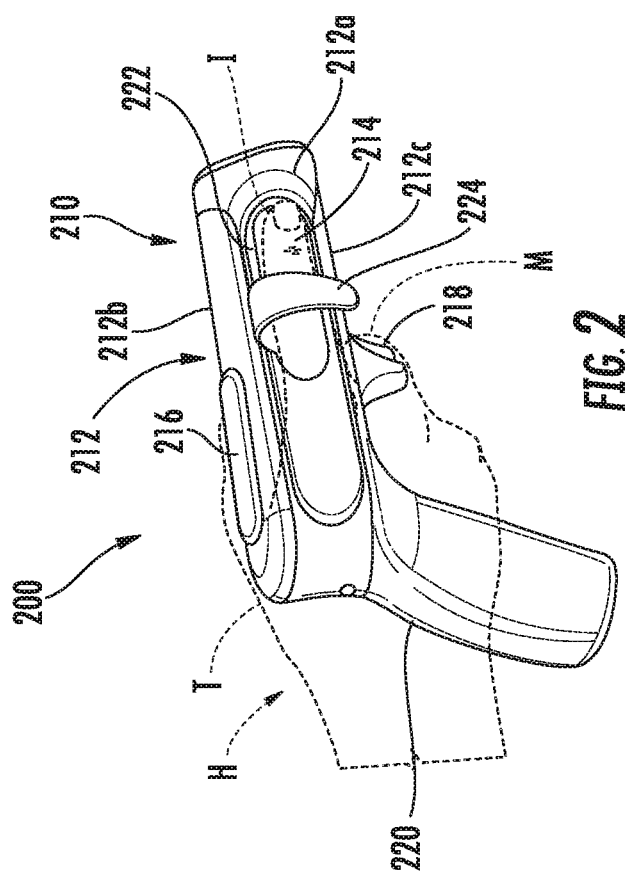
FIG. 3 is a perspective view of a tool of the robot system of the robotic surgical system of FIG. 1 in accordance with an embodiment of the present disclosure.
Figure 5:
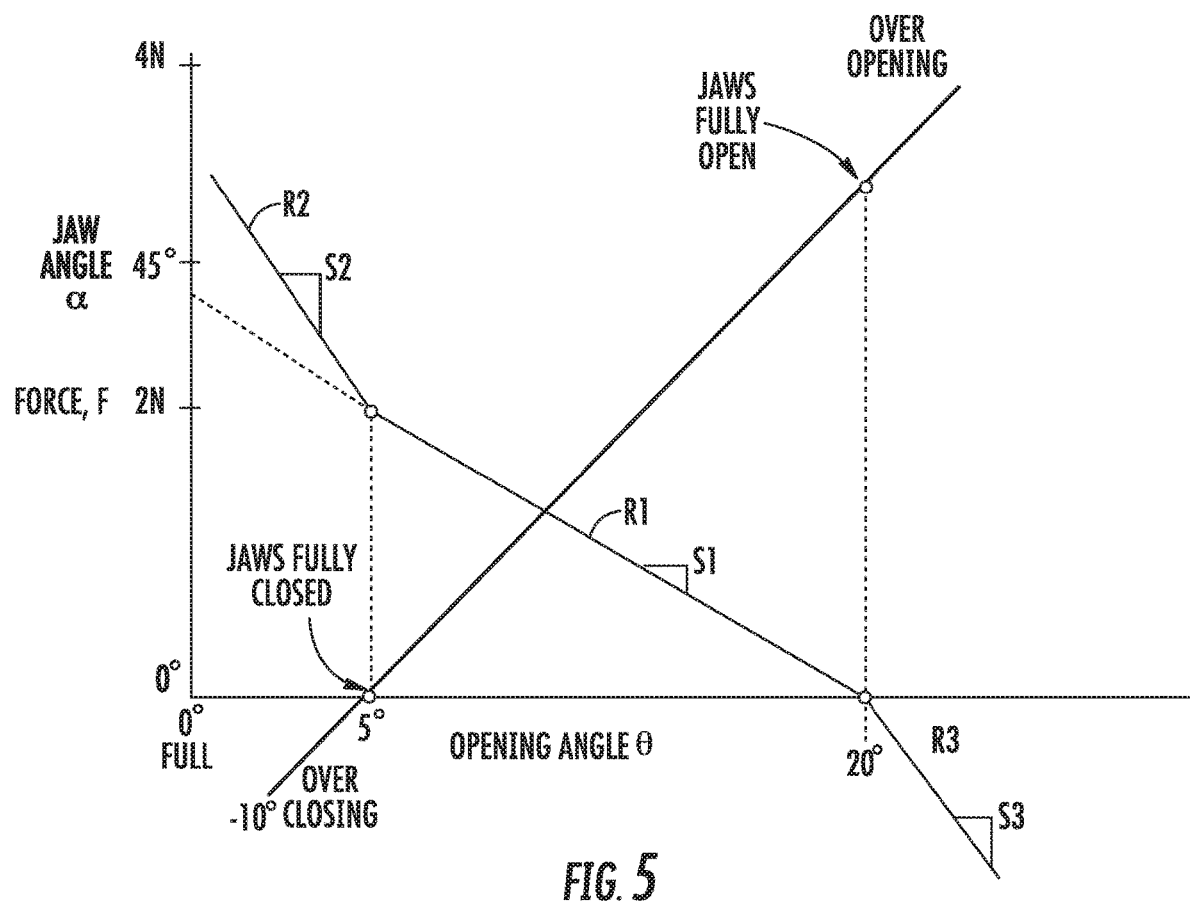
FIG. 5 is a graph showing jaw angle of the tool of FIG. 3 and force of a first actuator of the handle assembly of FIGS. 2 and 4 in response to changes in opening angle of the first actuator in accordance with an embodiment of the present disclosure.

With particular reference to FIG. 5, in conjunction with FIGS. 2 and 3, a graph of the jaw angle, $\alpha$, of the jaw assembly 20 as a function of the first actuator's opening angle, $\theta$, is shown. As discussed above, and shown in FIG. 5, the jaw members 22, 24 are fully open (e.g., disposed at a predetermined open angle greater than 0° with respect to each other) when the first actuator 214 has an opening angle, $\theta$, of about 20°, and the jaw members 22, 24 are fully closed (e.g., disposed at about a 0° angle with respect to each other) when the first actuator 214 has an opening angle, $\theta$, of about 5°. The jaw angle curve is linear such that changes in the opening angle, $\theta$, of the first actuator 214 (e.g., due to movement of the first actuator 214 by a clinician) produces a corresponding and directly proportional change in the jaw angle, $\alpha$, of the jaw assembly 20.

The jaw angle curve, however, does not cross the horizontal axis at the origin. Rather, the jaw angle curve crosses the horizontal axis when the opening angle, $\theta$, of the first actuator 214 is about 5° and the jaw members 22, 24 are disposed in the fully closed position. Such a configuration allows the jaw members 22, 24 to be fully closed before the first actuator 214 is fully pressed which may, for example, result in less finger fatigue of a clinician during use, and also allow the jaw members 22, 24 to over-close as the opening angle, $\theta$, approaches 0° (e.g., the first actuator 214 is fully pressed). Over-closing the jaw members 22, 24 increases the grasping force of the jaw assembly 20 which is desired for performing surgical tasks requiring a tight hold such as, for example, retraction of stiff tissues or needle driving. Similarly, the jaw members 22, 24 may over-open as the opening angle, $\theta$, is brought above 20°. Over-opening the jaw members 22, 24 increases the opening force of the jaw assembly 20 which is desired for performing surgical tasks requiring additional torque to open the jaw members 22, 24 such as, for example, tissue dissection.

It should be understood that the jaw angle curve may be modified to achieve different behaviors of the jaw members 22, 24 in response to changes in the opening angle, θ, of the first actuator 214. For example, the jaw angle curve may be a nonlinear curve having, for example, one or more shallow slopes at smaller opening angles, θ, of the first actuator 214 to provide better positional control of the jaw members 22, 24 as they approach the fully closed position, and one or more steeper slopes at larger opening angles, θ, of the first actuator 214 to increase the opening speed of the jaw members 22, 24 towards the fully open position. As another example, the jaw angle curve may include one or more flat regions that act as a holding region or detent to retain the jaw members 22, 24 in an intermediate position between being fully opened and fully closed. Such a jaw angle profile is useful for some tool types such as, for example, clip appliers when a clinician wants to hold and avoid dropping a clip. Accordingly, it is contemplated that the shape of the jaw angle curve may be different for different tool types or control modes utilized with the robotic surgical system 1.

With continued reference to FIG. 5, the force, F, profile of the first actuator 214 as a function of the opening angle, θ, of the first actuator 214 is also shown. As discussed above, the torque produced by the motor 232 generates the force, F, against which the first actuator 214 is pressed by a clinician to effect a change in the opening angle, θ, of the first actuator 214 and thus, the jaw angle, α, between the jaw members 22, 24. The force curve includes three linear regions "R1", "R2", and "R3", having different slopes "S1", "S2", and "S3", respectively. Region "R1" is defined in a portion of the force curve in which the jaw members 22, 24 are disposed between the fully open and fully closed positions. The slope "S1" of region "R1" is negative which causes the force, F, required to close the first actuator 214 to increase as the opening angle, θ, decreases. The force curve crosses the horizontal axis when the opening angle, θ, of the first actuator 214 is about 20° and the jaw members 22, 24 are disposed in the fully open position. Such a configuration allows the jaw members 22, 24 to open to the fully open position, corresponding to the biased position of the first actuator 214 detailed above, but not to over-open, when a clinician's finger is removed from the first actuator 214.

Region "R2" is defined in a portion of the force curve in which the jaw members 22, 24 are over-closed, and region "R3" is defined in a portion of the force curve in which the jaw members 22, 24 are over-opened. Slope "S2" of region "R2" is steeper or greater than slope "S1" of region "R1". Accordingly, as a clinician presses the first actuator 214 to close the jaw members 22, 24, the force, F, required to close the first actuator 214 increases as the first actuator 214 approaches region "R2" which, in turn, increases the stiffness in the first actuator 214 and provides a tactile indication to the clinician that the jaw members 22, 24 are entering or have entered the over-close region. Similarly, slope "S3" of region "R3" is steeper than slope "S1" of region "R1" to provide an indication to the clinician that the jaw members 22, 24 are entering or have entered the over-open region. All the values of the force, F, are negative in each of the regions "R1-R3" so that if the clinician's finger moves off of the first actuator 214, the jaw members 22, 24 move to the fully open position.

It should be understood that the force curve may be modified to achieve different behaviors of the first actuator 214 in response to changes in the opening angle, θ, of the first actuator 214 and/or to implement different desired features of the first actuator 214 and, in turn, the jaw members 22, 24. Accordingly, it is contemplated that the shape of the force curve may be different for different tool types or control modes.

Figure 6:
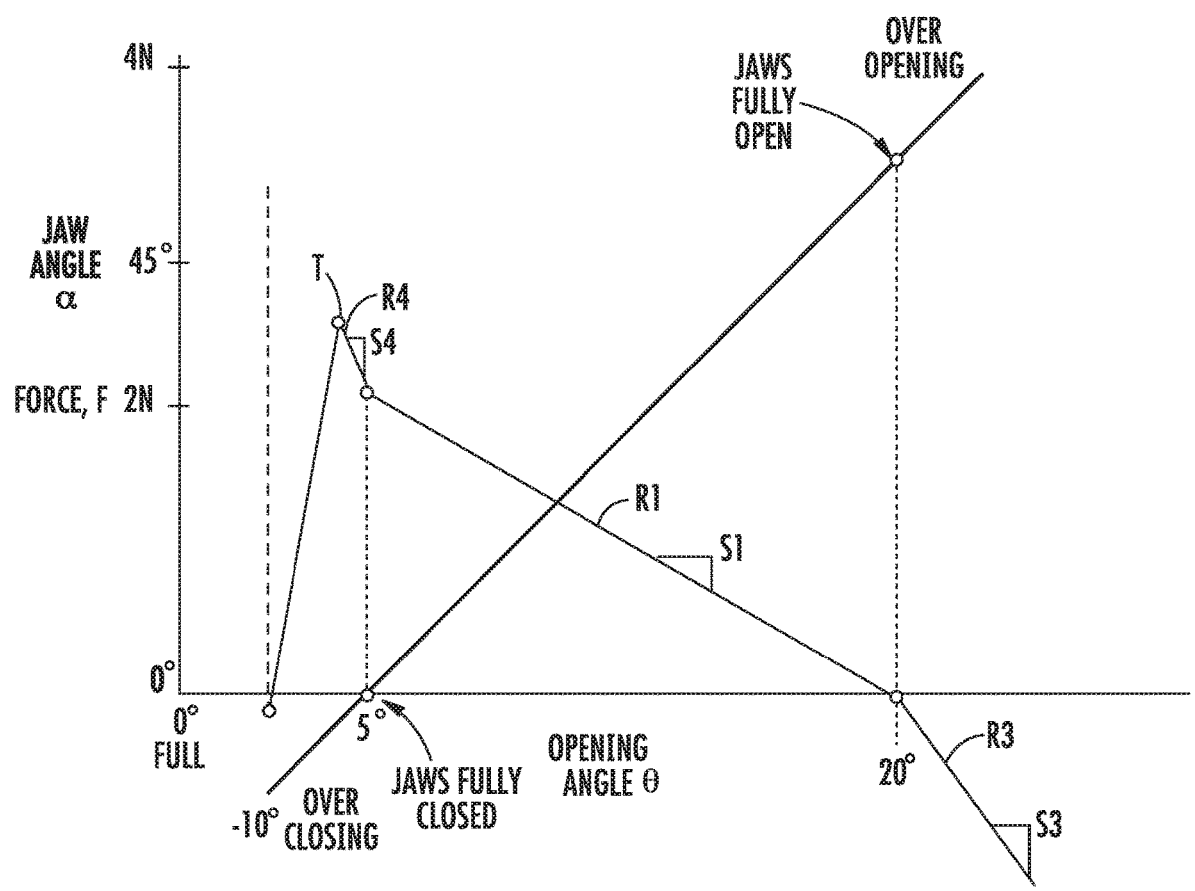
FIG. 6 is a graph showing jaw angle of the tool of FIG. 3 and force of a first actuator of the handle assembly of FIGS. 2 and 4 in response to changes in opening angle of the first actuator in accordance with another embodiment of the present disclosure.

For example, as shown in FIG. 6, a force curve includes three regions "R1", "R4", and "R3", having different slopes "S1", "S4", and "S3", respectively. Region "R4" is non-linear and includes a slope "S4" that is negative as the opening angle, θ, of the first actuator 214 approaches 0°. Accordingly, when a clinician presses the first actuator 214 to over-close the jaw members 22, 24 and approaches a torque transition point "T" associated with an opening angle, θ, of the first actuator 214, negative torque from the motor 232 closes the opening angle, θ, of the first actuator 214 which, in turn, causes the jaw members 22, 24 to snap to and remain in the over-closed position, even if the clinician's finger is removed from the first actuator 214. Such a configuration retains the first actuator 214 in the closed position to assist the clinician in holding the first actuator 214 and thus, the jaw members 22, 24 in the over-closed position. This behavior assists a clinician while performing surgical tasks such as, for example, suturing, which requires holding a needle tightly between the jaw members 22, 24 while performing complex, dexterous maneuvers with the handle assembly 200 (FIG. 1). The clinician can relax his or her grip on the first actuator 214 during these tasks which can improve ergonomics, reduce fatigue, and/or increase control of the position and orientation of the tool 20 (FIG. 1).

To open the jaw members 22, 24, the clinician overpowers the negative torque of the motor 232 and opens the first actuator 214 until the torque switches to a positive value. This may be done by, for example, pulling the first actuator away using the strap or the like.

The force profile, F, of the first actuator 214 behaves as shown in FIG. 5 in regions "R1" and "R3". For example, when the opening angle, θ, of the first actuator 214 is between about 5° and 20°, and the jaw members 22, 24 are between the fully open and fully closed positions, the clinician can open and close the jaw members 22, 24 to intermediate position(s) as desired.

Figure 7:
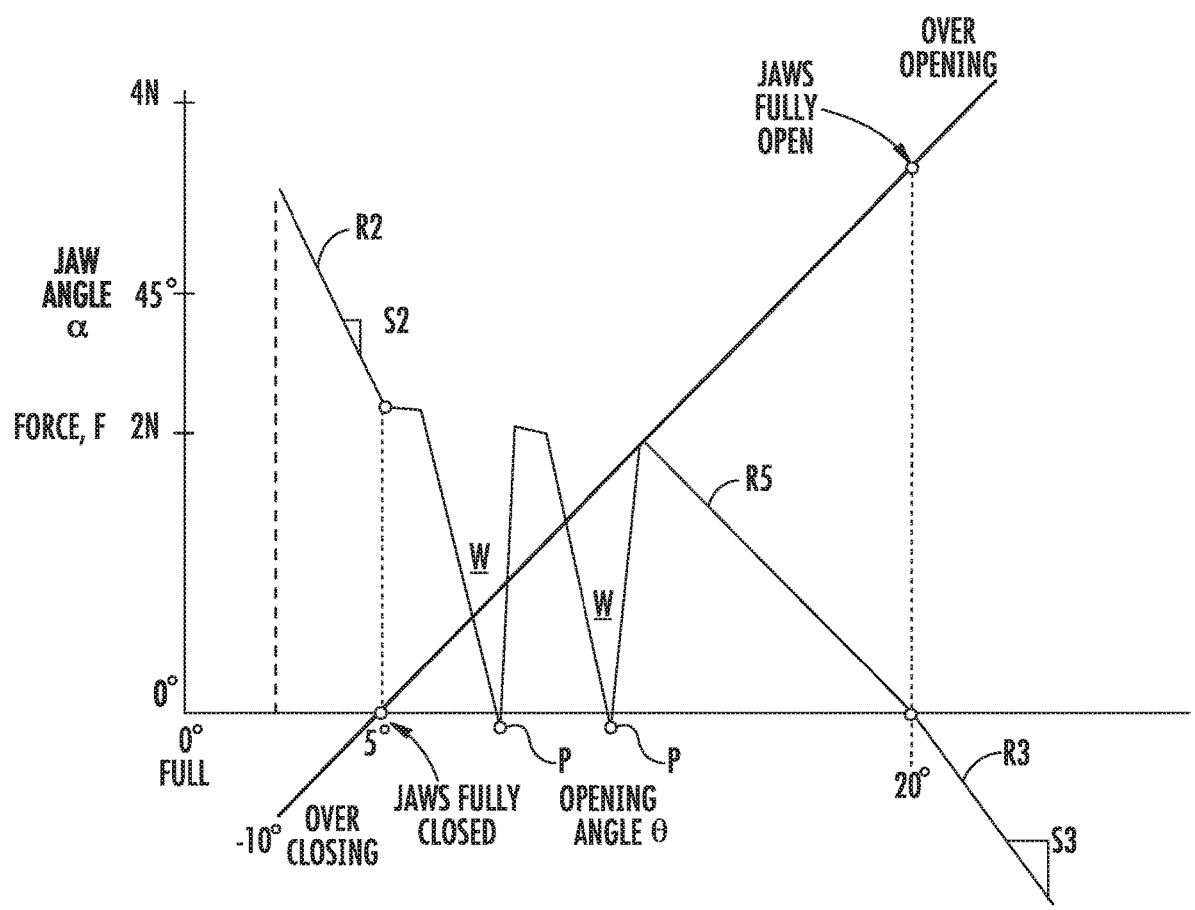
FIG. 7 is a graph showing jaw angle of the tool of FIG. 3 and force of a first actuator of the handle assembly of FIGS. 2 and 4 in response to changes in opening angle of the first actuator in accordance with yet another embodiment of the present disclosure.

As another example, as shown in FIG. 7, a force curve or profile includes three regions "R5", "R2", and "R3". The force profile, F, of the first actuator 214 behaves as shown in FIG. 5 in regions "R2" and "R3". Region "R5" (e.g., the portion of the force curve in which the jaw members 22, 24 are disposed between the fully open and fully closed positions) is a non-linear region including a plurality of torque wells "W" defined at predefined opening angles, θ, of the first actuator 214 (and thus, predefined jaw angles, α, of the jaw assembly 20) that are configured to hold and maintain the corresponding opening angle, θ, of the first actuator 214. The torque wells "W" define positive to negative torque transition points "P" which causes the motor 232 of the handle controller 230 to snap to and maintain the corresponding opening angle, θ, of the first actuator 214 which, in turn, maintains the corresponding jaw angle, α, of the jaw members 22, 24 even if the clinician's finger is removed from the first actuator 214. In use, the first actuator 214 provides a tactile indication (e.g., a snap) to alert the clinician that the jaw members 22, 24 are being held at the predefined jaw angle, α. To move the actuator 214, the clinician pushes or pulls the first actuator 214 in or out of the torque wells "W" to cause the jaw members 22, 24 to move through their full range of motion.

The torque wells "W" may correspond with important use locations of the tool 20. For example, the motion of the first actuator 214 may be mapped to the advancement of a stapler blade and the torque wells "W" indicate a predetermined increment (e.g., 1 cm) of travel. As another example, the torque wells "W" may be used to set various opening angles for a grasper so that a clinician can more precisely control and maintain a grasping force with the grasper.

While the embodiments above are described with respect to controlling the jaw angle of a jaw assembly through actuation of a first actuator in the form of a paddle (e.g., adjusting the force profile of the first actuator as a function of the opening angle of the first actuator), it should be understood that various tools and/or other actuator configurations may be utilized. For example, the actuator may be longitudinally translatable (e.g., in the form of a button or slide) such that positional movement measured by the microcontroller would be a translational position of the actuator. The jaw angle and force would change based on changes in the translational position of the actuator. As another example, functions other than jaw angle may be changed in response to actuation of the actuator (e.g., movement of a blade). It should be further understood that the processing unit and/or handle controller may be configured to identify the tool associated with the handle assembly to implement jaw angle and force curve profiles desired for use with the tool.

As detailed above and shown in FIG. 1, the user interface 40 is in operable communication with the robot system 10 to perform a surgical procedure on a patient "P"; however, it is envisioned that the user interface 40 may be in operable communication with a surgical simulator (not shown) to virtually actuate a robot system and/or tool in a simulated environment. For example, the surgical robot system 1 may have a first mode where the user interface 40 is coupled to actuate the robot system 10 and a second mode where the user interface 40 is coupled to the surgical simulator to virtually actuate a robot system. The surgical simulator may be a standalone unit or be integrated into the processing unit 30. The surgical simulator virtually responds to a clinician interfacing with the user interface 40 by providing visual, audible, force, and/or haptic feedback to a clinician through the user interface 40. For example, as a clinician interfaces with the handle assemblies 200, the surgical simulator moves representative tools that are virtually acting on tissue at a simulated surgical site.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and within the scope of this disclosure and the appended claims. Therefore, the above description should not be construed as limiting, but merely as exemplifications of particular embodiments. Those skilled in the art will envision other modifications within the scope of the claims appended hereto.

What is claimed is:

1. A robotic surgical system comprising:
   a robotic arm supporting a jaw assembly, the jaw assembly including opposed jaw members defining a jaw angle therebetween; and
   a user interface including a handle assembly, the handle assembly including:
     a body portion;
     a handle controller disposed within the body portion; and
     a first actuator movable relative to the body portion to change an opening angle of the first actuator, the first actuator having a force profile which is a force required to move the first actuator as a function of the opening angle, and the jaw assembly having a jaw angle profile which is the jaw angle as a function of the opening angle.

2. The robotic surgical system according to claim 1, wherein the jaw angle profile defines a jaw angle curve, and wherein a microcontroller of the handle controller is configured to transmit the opening angle of the first actuator to the robotic arm to effect a change in the jaw angle of the jaw members based on the jaw angle curve.

3. The robotic surgical system according to claim 2, wherein the jaw angle curve is linear.

4. The robotic surgical system according to claim 3, wherein as the opening angle of the first actuator decreases, the jaw angle of the jaw members decreases.

5. The robotic surgical system according to claim 1, wherein the force profile defines a force curve, and wherein a microcontroller of the handle controller is configured to record the opening angle of the first actuator and adjust operating parameters of a motor of the handle controller to effect a change in the force required to actuate the first actuator based on the force curve.

6. The robotic surgical system according to claim 5, wherein a portion of the force curve has a negative slope in which the force increases as the opening angle decreases.

7. The robotic surgical system according to claim 5, wherein a portion of the force curve has a positive to negative slope transition point at a predetermined opening angle of the first actuator, the motor producing a torque to maintain the first actuator at the predetermined opening angle.

8. The robotic surgical system according to claim 1, wherein the first actuator has an open position in which the opening angle is a first open angle and a closed position in which the opening angle is a second open angle less than the first open angle, and wherein the force profile has a first region defined between the first open angle and a third open angle that is less than the first open angle and greater than the second open angle.

9. The robotic surgical system according to claim 8, wherein the jaw members have a fully open position and a fully closed position, the jaw members disposed in the fully open position when the opening angle of the first actuator is at the first open angle and in the fully closed position when the opening angle of the first actuator is at the third open angle.

10. The robotic surgical system according to claim 9, wherein the force profile has a second region defined between the second open angle and the third open angle, the jaw members disposed in an over-closed position when the opening angle of the first actuator is between the second and third open angles.

11. The robotic surgical system according to claim 10, wherein the force profile has a third region in which the opening angle of the first actuator is greater than the first open angle, the jaw members disposed in an over-open position when the opening angle of the first actuator is greater than the first open angle.

12. The robotic surgical system according to claim 11, wherein the first region of the force profile is linear and has a first negative slope such that the force increases as the opening angle decreases in the first region.

13. The robotic surgical system according to claim 12, wherein the second region of the force profile is linear and has a second negative slope greater than the first negative slope.

14. The robotic surgical system according to claim 13, wherein the third region of the force profile is linear and has a third negative slope greater than the first negative slope, and wherein when no force is applied to the first actuator, the first actuator is biased towards the first open angle.

15. The robotic surgical system according to claim 13, wherein the second region includes a torque transition point at a predetermined opening angle of the first actuator such that when the first actuator is moved to the predetermined opening angle, the motor of the handle controller produces a torque to maintain the first actuator at the predetermined opening angle.

16. The robotic surgical system according to claim 11, wherein the first region of the force profile is non-linear.

17. The robotic surgical system according to claim 16, wherein the first region of the force profile includes a positive to negative torque transition point at a predetermined opening angle of the first actuator such that when the first actuator is moved to the predetermined opening angle, the motor of the handle controller produces a torque to maintain the first actuator at the predetermined opening angle.

* * * * *